United States Patent [19]

Gleich et al.

[11] Patent Number: 5,631,267
[45] Date of Patent: *May 20, 1997

[54] METHOD FOR THE TREATMENT OF EOSINOPHIL-ASSOCIATED DISEASES BY ADMINISTRATION OF TOPICAL ANESTHETICS

[75] Inventors: Gerald J. Gleich, Rochester, Minn.; Tsukasa Ohnishi, Tokyo, Japan; Loren W. Hunt, Rochester, Minn.

[73] Assignee: Mayo Foundation For Medical Education & Research, Rochester, Minn.

[*] Notice: The term of this patent shall not extend beyond the expiration date of Pat. No. 5,510,339.

[21] Appl. No.: 618,860

[22] Filed: Mar. 20, 1996

Related U.S. Application Data

[63] Continuation of Ser. No. 12,343, Feb. 2, 1993, Pat. No. 5,510,339.
[51] Int. Cl.$^6$ .................. A61K 31/47; A61K 31/24; A61K 31/16
[52] U.S. Cl. .................. 514/312; 514/317; 514/330; 514/535; 514/540; 514/626; 514/826; 514/914
[58] Field of Search .................. 514/626, 826, 514/914, 312, 317, 330, 535, 540

[56] References Cited

U.S. PATENT DOCUMENTS

| | | | |
|---|---|---|---|
| 4,466,973 | 8/1984 | Rennie | 424/267 |
| 4,626,530 | 12/1986 | Schulte | 514/166 |
| 4,748,022 | 5/1988 | Busciglio | 424/195.1 |
| 5,134,166 | 7/1992 | Bernstein | 514/627 |

FOREIGN PATENT DOCUMENTS

3385  6/1965  France .

OTHER PUBLICATIONS

G.H. Ayers et al., "Injurious Effect of the Eosinophil Peroxide–Hydrogen Peroxide–Halide System and Major Basic Protein on Human Nasal Epithelium in vitro", *Am. Rev. Resp. Dis.*, 140:125 (1989).
P.J. Barnes, *The Lancet*, 242 (Feb. 1, 1986).
R. Bascom et al., "Major Basic Protein and Eosinophil–Derived Neurotoxin Concentrations in Nasal–Lavage Fluid After Antigen Challenge: Effect of Systemic Corticosteroids and Relationship to Eosinophil Influx", *J. Allergy Clin. Immunol.*, 84:338 (1989).
J.H. Butterfield et al., "Chapter 8: Anti–Inflammatory Effects of Glucocorticoids on Eosinophils and Neutrophils", *Anti–Inflammatory Steroid Action: Basic and Clinical Aspects*, Schleimer et al., editors, Academic Press Inc., at pages 151–198 (1980).
W.Y. Chen et al., "Effects of Inhaled Lidocaine on Exercise–Induced Asthma", *Respiration*, 51, pp. 91–97, (1987).
H. Downes et al., "Lidocaine Aerosols Do Not Prevent Allergic Bronchoconstriction", *Anesth. Analg.*, 60, pp. 28–32, (1981).

M.S. Dunnill, "The Pathology of Asthma, with Special Reference to Changes in the Bronchial Mucosa", *J. Clin. Path.*, 13:27 (1960).
A.G. Ellis et al., "The Pathological Anatomy of Bronchial Asthma", *J. Med. Sci.*, 136:407 (1980).
P.L. Enright et al., *Am. Rev. Resp. Disease*, 172, 823 (1980).
W. Filley et al., "Identification by Immunofluorescence of Eosinophil Granule Major Basic Protein in Lung Tissues of Patients with Bronchial Asthma", *Lancet*, 2:11 (1982).
E. Frigas et al., "Cytotoxic Effects of the Guinea Pig Eosinophil Major Basic Protein on Tracheal Epithelium", *Lab. Invest.*, 42:35 (1980).
E. Frigas et al., "Elevated Levels of The Eosinophil Granule Major Basic Protein in the Sputum of Patients with Bronchial Asthma", *Mayo Clinic. Proc.*, 56:345 (1981).
T. Fujisawa et al., "Regulatory Effects of Cytokines on Eosinophil Degranulation", *J. Immunol.*, 144:642 (1990).
G.J. Gleich, "Identification of a Major Basic Protein in Guinea Pig Eosinophil Granules", *J. Exp. Med.*, 137:1459 (1973).
G.J. Gleich et al., "Cytotoxic Properties of the Eosinophil Major Basic Protein", *J. Immunol.*, 123:2925 (1979).
G.J. Gleich et al., "The Eosinophilic Leukocyte: Structure and Function", *Adv. Immunol.*, 39:177–253 (1986).
N.J. Gross et al., "Chapter 34: Anticholinergic Drugs", *Allergy, Principles and Practice*, vol. I, at pp. 782–808, E. Middleton Jr. et al., ed., The C.V. Mosby Company, publisher, (1988).
R.H. Gundel et al., "Repeated Antigen Inhalation Results in a Prolonged Airway Eosinophilia and Airway Eosinophilia and Airway Hyperresponsiveness in Primates", *J. Appl. Physiol.*, 68:779 (1990).
Q. Hamid et al., "Expression of mRNA for Interleukin–5 in Mucosal Bronchial Biopsies from Asthma", *J. Clin. Invest.*, 87:1541 (1991).
S.L. Harlin et al., "A Clinical and Pathologic Study of Chronic Sinusitis: The Role of the Eosinophil", *J. Allergy Clin. Immunol.*, 81:867 (1988).
A.T. Hastie et al., "The Effect of Purified Human Eosinophil Major Basic Protein on Mammalian Ciliary Activity", *Am. Rev. Resp. Dis.*, 135:845 (1987).
B.R. Horn et al., "Total Eosinophil Counts in the Management of Bronchial Asthma", *N. Engl. J. Med.*, 292:1152 (1975).
M. Krasnowska et al., "A Test of Lidocaine Usage in the Treatment of Bronchial Asthma", *Pneum. Pol.*, 50, pp. 269–273, (1982).

(List continued on next page.)

*Primary Examiner*—Raymond Henley, III
*Attorney, Agent, or Firm*—Schwegman, Lundberg, Woessner & Kluth, P.A.

[57] ABSTRACT

A therapeutic method is provided to treat eosinophil-associated hypersensitivity diseases, such as bronchial asthma, by locally administering to a mammal in need of such treatment, an effective amount of a topical anesthetic, such as lidocaine, or a pharmaceutically acceptable salt thereof.

15 Claims, 4 Drawing Sheets

OTHER PUBLICATIONS

A.M. Lamas et al., "Glucocorticoids Specifically Decrease Eosinophil Survival", *J. Allergy Clin. Immunol.*, 85:282, Abstract No. 554 (1990).

A.M. Lamas et al., "Glucocorticoids Specifically Decrease Eosinophil Survival", *J. Immunol.*, 142:3978 (1989).

P.J. Mauser et al., "The Effect of Anti–Il–5 on Antigen–Induce Airway Hyperreactivity and Pulmonary Eosinophilia in Guinea Pigs", *Am. Rev. Respir. Dis.*, 145:A859 (1992).

S. Motojima et al., "Toxicity of Eosinophil Cationic Proteins for Guinea Pig Tracheal Epithelium in Vitro", *Am. Rev. Resir. Dis.*, 139:801 (1989).

M.E. Rothenberg et al., "Human Eosinophil have Prolonged Survival, Enhanced Functional Properties, and Become Hypodense when Exposed to Human Interleukin 3", *J. Clin. Invest.*, 81:1986 (1988).

V.N. Saperov, "The Treatment of Bronchial Asthma with the Aid of Intra–Arterial Injections of Novocain", *Klin. Med.*, 45, pp. 50–54 (1967).

R.P. Schleimer et al., "Effects of Glucocorticosteroids on Inflammatory Cells Relevant to Their Therapeutic Applications in Asthma", *Am. Rev. Respir. Dis.*, 141:559 (1990).

J.B. Sedgwich et al., "Immediate and Late Airway Response of Allergic Rhinitis Patients to Segmental Antigen Challenge", *Am. Rev. Respir. Dis.*, 144:1274 (1991).

R. Sehmi et al., "Interleukin–5 Selectively Enhances the Chemotactics Response of Eosinophils Obtained from Normal but not Eosinophilic Subjects", *Blood*, 79:2952 (1992).

D.S. Silberstein et al., "Enhancement of Human Eosinophil Cytotoxicity and Leukotriene Synthesis by Biosynthetic (Recombinant) Granulocyte–Macrophage Colony–Stimulating Factor", *J. Immunol.*, 137:3290 (1986).

D.S. Silberstein et al., "Hemopoietins for Eosinophils", *Hematol. Oncol. Clin. North Am.*, 3:511 (1989).

S.D. Trocme et al., "Conjunctival Deposition of Eosinophil Granule Major Basic Protein in Vernal Keratoconjunctivitis and Contact Lens–Associated Giant Papillary Conjunctivitis", *Am. J. Ophthamol.*, 108:57 (1989).

W.M. Tullett et al., *Thorax*, 37, 737 (1982).

I.J. Udell et al., "Eosinophil Granule Major Basic Protein and Charcot–Leyden Crystal Protein in Human Tears", *Am. J. Ophthamol.*, 92:824 (1981).

T. Valerius et al., "Effects of IFN on Human Eosinophils in Comparison with Other Cytokines", *J. Immunol.*, 145:2950 (1990).

N. Wallen et al., "Glucocorticoids Inhibit Cytokine–Mediated Eosinophil Survival", *J. Immunol.*, 147:3940 (1991).

A.J. Wardlaw et al., "Eosinophils and Mast Cells in Bronchoalveolar Lavage in Subjects with Mild Asthma", *Am. Rev. Resp. Dis.*, 137:62 (1988).

T.L. Wasmoen et al., "Biochemical and Amino Acid Sequence Analysis of Human Eosinophil Granule Major Basic Protein", *J. Biol. Chem.*, 263:12559 (1988).

*Merck Manual*, pp. 622–627, (1982).

*Remington's Pharmaceutical Sciences*, pp. 1051–1052 (1985).

METHOD FOR THE TREATMENT OF EOSINOPHIL-ASSOCIATED DISEASES BY ADMINISTRATION OF TOPICAL ANESTHETICS

This invention was made with the assistance of the United States Public Health Service under grant number AI-15231. The U.S. Government has certain rights in the invention.

This application is a continuation of U.S. patent application Ser. No. 08/012,343, filed on Feb. 2, 1993, now U.S. Pat. No. 5,510,339.

BACKGROUND OF THE INVENTION

For many years, bronchial asthma was regarded as an abnormality of respiratory smooth muscle in which afflicted individuals experience the onset of bronchospasm as a consequence of overreactivity of the bronchial smooth muscle. Later, the bronchial mast cell was thought to play a critical role in the stimulation of bronchial smooth muscle by producing leukotriene C4 (the slow-reacting substance of anaphylaxis) and histamine, which cause contraction. However, over the past few years, a dramatic change in thinking regarding the pathophysiology of bronchial asthma has occurred and the involvement of eosinophilic leukocytes, or "eosinophils," in the inflammation of the airway has been suspected.

Eosinophils are a type of leukocyte containing cytoplasmic granules that stain strongly with acidic dyes. Eosinophils have been associated with bronchial asthma since the early part of this century and they are characteristically found in large numbers in the lung tissue of patients dying of asthma (A. G. Ellis et al., *J. Med. Sci.*, 136, 407 (1908)). In the mid 1970s, it was demonstrated that the severity of bronchial asthma can be related to the number of eosinophils in the peripheral blood of the patients (B. R. Horn et al., *N. Engl. J. Med.*, 292, 1152 (1975)). Also around this time, studies of eosinophils had shown the presence of basic (cationic) granule proteins. One of the principal proteins associated with eosinophil granules, the major basic protein (MBP), was so-named because, in the guinea pig, it comprises more than 50% of the granule protein, is strongly basic (arginine-rich), and is proteinaceous (G. J. Gleich, *J. Exp. Med.*, 137, 1459 (1973); T. L. Wasmoen et al., *J. Biol. Chem.*, 263, 12559 (1988)). MBP is toxic to worms (helminths) and mammalian cells, and causes damage to bronchial respiratory epithelium (G. J. Gleich et al., *Adv. Immunol.*, 39, 177 (1986)). For example, direct application of MBP to respiratory epithelium in concentrations as low as 10 µg/ml ($7.1 \times 10^{-7}$M) causes ciliostasis and epithelial damage. This damage consists of desquamation of epithelial cells into the lumen of the respiratory tract, as well as frank disruption of epithelial cells. The effects of MBP are dose-related and higher doses cause damage more quickly and to a greater extent than lower doses (E. Frigas et al., *Lab. Invest.*, 42, 35 (1980)). These effects are caused both by MBP from guinea pig eosinophils and from human eosinophils, and impact both guinea pig and human respiratory tissues (G. J. Gleich et al., *J. Immunol.*, 123, 2925 (1979)).

The findings that MBP causes ciliostasis, desquamation of respiratory epithelial cells, and damage to the respiratory epithelial cells are suggestive of the pathologic changes observed in bronchial asthma. In bronchial asthma, an exudate of eosinophils, normal and degenerating bronchial epithelial cells, and clumps of epithelial cells, referred to as Creola bodies, are present in the bronchial lumen. In the bronchial mucosa and submucosa, edema, separation and shedding of ciliated cells, and eosinophil infiltration are seen. Thus, the effects of the eosinophil granule MBP in vitro are similar to the pathology characteristic of bronchial asthma (M. S. Dunnill, *J. Clin. Path.*, 13, 27 (1960)).

Because of this discovery, the levels of MBP in sputum of patients with bronchial asthma were measured to determine whether they were elevated and to what degree. Levels of MBP in sputum samples from 206 patients with various respiratory diseases were measured by radioimmunoassay. In 165 of these patients, MBP was not measurable or the concentrations of MBP were less than 0.1 µg/ml. In these 165 patients, only one patient carried the diagnosis of asthma. Among 41 patients with sputum concentrations of MBP greater than 0.1 µg/ml, 28 were diagnosed as having asthma and in the remaining 13 patients, six had obstructive lung disease which is often confused with asthma. In 15 patients hospitalized for treatment of asthma, sputum MBP levels ranged from 0.5 ($0.04 \times 10^{-6}$M) to 93 µg/ml ($6.6 \times 10^{-6}$M) (geometric mean 7.1 µg/ml, $0.51 \times 10^{-6}$M). Further, the levels of sputum MBP in these 15 patients declined during therapy with glucocorticoids (E. Frigas et al., *Mayo Clinic. Proc.*, 56, 345 (1981)). These results indicated that MBP levels in the toxic range were present in the sputum of patients with asthma, that levels of sputum MBP were highest in acutely ill patients, and that sputum MBP levels decline after steroid therapy.

The possibility that MBP directly causes damage to bronchial epithelium was tested utilizing immunofluorescence localization of MBP in lung tissues of patients dying of asthma (W. Filley et al., *Lancet*, 2, 11 (1982)). These results showed that the patients dying of asthma had the classical pathologic features of bronchial asthma with a thickened basement membrane zone, goblet cell hyperplasia, and peribronchial inflammatory infiltrates with eosinophils in the lamina propria. Examination of these same sections by immunofluorescence to localize MBP, revealed MBP deposition onto damaged bronchial epithelium. These results demonstrate that MBP was released from the eosinophil and was present in tissues at the site of damage.

Subsequent studies extended these observations showing that not only MBP, but two of the other cationic eosinophil granule proteins, namely eosinophil peroxidase (EPO) and eosinophil cationic protein (ECP), have the capacity to damage bronchial epithelium (S. Motojima et al., *Am. Rev. Respir. Dis.*, 139, 801 (1989)). Analyses of the effect of MBP on respiratory epithelium showed that although MBP reduced the frequency of ciliary beating, its predominant effect was to reduce the number of beating ciliated cells. The effect of MBP in causing cessation of ciliary beating was seen in respiratory epithelial cells in the epithelium itself as well as in axonemes (the contractile elements of the cilia) (A. T. Hastie et al., *Am. Rev. Resp. Dis.*, 135, 845 (1987)).

One of the signal abnormalities in bronchial asthma is bronchial hyperreactivity. Bronchial hyperreactivity is manifested in patients as a marked irritability of the respiratory tract to nonspecific stimuli including cold air, dust, and, in the laboratory, to inhaled methacholine. Indeed, this hyperreactivity is a diagnostic criterion for asthma (N. J. Gross et al., in *Allergy, Principles and Practice*, Vol. I., E. Middleton, Jr. et al., eds. (1988) at page 790). Analyses of MBP in the lung secretions of patients with asthma (obtained by lavage of the bronchi and alveoli) showed that MBP levels in lung fluids are correlated with bronchial hyperreactivity (A. J. Wardlaw et al., *Am. Rev. Resp. Dis.*, 137, 62

(1988)). In cynomolgus monkeys, provocation of inflammation rich in eosinophils was associated with an increase in bronchial hyperreactivity and with the presence of MBP in lung secretions; both the numbers of eosinophils and the MBP concentration were significantly correlated with bronchial hyperreactivity to methacholine (R. H. Gundel et al., *J. Appl. Physiol.*, 68 779 (1990)).

At the molecular level, eosinophil proliferation and differentiation are regulated by various cytokines, such as IL-3, IL-5 and GM-CSF. See D. S. Silberstein et al., *Hematol. Oncol. Clin. North Am.*, 3, 511 (1989). These cytokines, as well as IFN-γ, have been shown to prolong survival of eosinophils in vitro by T. Valerius et al., *J. Immunol.*, 145, 2950 (1990), and to augment eosinophil function (M. E. Rothenberg et al., *J. Clin. Invest.*, 81 1986 (1988); T. Fujisawa et al., *J. Immunol.*, 144, 642 (1990); D. S. Silberstein et al., *J. Immunol.*, 137, 3290 (1986)). Furthermore, IL-5 primes eosinophils for enhanced locomotor responses to chemotactic agents, such as platelet-activating-factor, leukotriene B4, and IL-8 (R. Sehmi et al., *Blood*, 79, 2952 (1992)). Also, recent information indicates that IL-5 is present in the lung following allergen-induced pulmonary late allergic reactions (J. B. Sedgwick et al., *Am. Rev. Respir. Dis.*, 144, 1274 (1991) and mRNA for IL-5 is expressed in the bronchial epithelium of patients with asthma (Q. Hamid et al., *J. Clin. Invest.*, 87, 1541 (1991)). These observations suggest that the inflammation associated with asthma is critically dependent on the presence of cytokines, especially IL-5, and recent data showing that antibodies to IL-5 block both antigen-induced eosinophilia and antigen-induced bronchial hyperreactivity support that view (P. J. Mauser et al., *Am. Rev. Respir. Dis.*, 145, A859 (1992)).

Glucocorticoids are the most useful class of drugs for treating many eosinophil-related disorders, including bronchial asthma (R. P. Schleimer et al., *Am. Rev. Respir. Dis.*, 141, 559 (1990)). They produce eosinopenia in normal persons, decrease circulating eosinophils in patients with eosinophilia, and reduce eosinophil influx at inflammatory sites (J. H. Butterfield et al., in *Antiinflammatory Steroid Action: Basic and Clinical Aspects*, R. P. Schleimer et al., eds., Academic Press, Inc. (1989) at p. 151. The mechanism of these effects is still uncertain. Lamas et al. in *J. Immunol.*, 142, 3978 (1989) and *J. Allergy Clin. Immunol.*, 85, 282 (1990) have reported that supernatants from human vascular endothelial cells cultured with glucocorticoids had reduced eosinophil survival-enhancing activity in vitro.

Recently, N. Wallen et al., *J. Immunol.*, 147, 3940 (1991) reported the dose-dependent inhibition of IL-5-mediated eosinophil survival by dexamethasone, methylprednisolone and hydrocortisone, and the inhibition of IL-3-, GM-CSF-, and IFN-γ-mediated eosinophil survival by dexamethasone. Dexamethasone produced a dose-dependent increase in the $EC_{50}$ for IL-5-mediated viability enhancement. The relative eosinophil viability inhibitory potencies of the glucocorticoids tested correlated with previously described antiinflammatory potencies and with the affinities for the glucocorticoid receptor: dexamethasone>methylprednisolone>hydrocortisone.

However, for many patients with asthma, glucocorticoids are the principal therapy and these patients may require glucocorticoid therapy for long periods of time, e.g., months to years. In fact, the disease can be characterized as one of chronic glucocorticoid toxicity, in that the toxicity of these steroids can cause severe morbidity and even mortality in the patients. Furthermore, cessation of glucocorticoid therapy leads to withdrawal symptoms, such as malaise and muscle pain. However, presently glucocorticoids are the only effective therapy for severe asthma, and are prescribed long-term despite their toxicity.

The information discussed above pertains to bronchial asthma and the role of toxic eosinophil granule proteins exemplified by MBP in the pathophysiology of bronchial asthma. Evidence exists that these toxic proteins also contribute to the pathogenesis of diseases associated with eosinophil infiltration in the upper respiratory tract. For example, G. H. Ayars et al. in *Am. Rev. Resp. Dis.*, 140, 125 (1989), have reported that MBP is toxic to respiratory epithelium from the nose, and R. Bascom et al., in *J. Allergy Clin. Immunol.*, 84, 338 (1989) found that elevated MBP concentrations are present in nasal fluids following experimental hay fever. As reported by S. L. Harlin et al., *J. Allergy Clin. Immunol.*, 81, 867 (1988), MBP is deposited on respiratory epithelium of the upper airway in association with damage to the epithelium. Therefore, toxic eosinophil granule proteins may cause disease of the upper airway in the same manner as they likely do in the lower airway in the case of bronchial asthma.

Finally, I. J. Udell et al., in *Am. J. Ophthamol.*, 92, 824 (1981) reported that MBP is elevated in tears of patients with vernal conjunctivitis, a form of allergic inflammation of the eye, and S. D. Trocme et al., in *Am. J. Ophthamol.*, 108, 57 (1989) found that MBP is deposited into inflamed conjunctiva of such patients. Thus, evidence exists that MBP may act as a toxin to the conjunctiva.

Therefore, a need exists for improved therapeutic methods to treat hypersensitivity diseases, such as bronchial asthma, which are caused by, or aggravated by, eosinophils or the toxic proteins released by eosinophils.

SUMMARY OF THE INVENTION

The present invention provides a method for treating a hypersensitivity disease, such as bronchial asthma, comprising administering to a mammal, such as a human, afflicted with such a disease, an amount of a topical anesthetic or a pharmaceutically acceptable salt thereof, effective to counteract the symptoms of the disease. The topical anesthetics useful in the present invention are believed to act directly or indirectly so as to prevent eosinophil accumulation and activation. It is believed that the topical anesthetic or salt thereof acts by counteracting the effects of eosinophil-active cytokines, such as IL-5, on eosinophils resident in the lungs of the human.

A preferred embodiment of the present method is directed to a therapy for bronchial asthma, eosinophil-associated intranasal inflammation, including nasal polyps, inflammation of the paranasal sinuses and allergic rhinitis, and eosinophil-associated inflammation of the eye, such as vernal and allergic conjunctivitis. The present method involves counteracting or preventing the symptomologies caused by eosinophils at the site of inflammation by the local administration of effective amounts of one or more topical anesthetics to the afflicted or susceptible human. For example, the present invention provides a therapy for bronchial asthma and the other hypersensitivity diseases of the respiratory tract, by administration by inhalation or insufflation of a topical anesthetic, such as lidocaine, bupiracaine, etidocaine, tetracaine and the like. The topical anesthetic in turn is able to inhibit the activity of eosinophil-active cytokines, such as IL-5, and thus to limit the negative effects of eosinophils on respiratory epithelium or other tissue. Topical administration of a topical anesthetic, e.g., in nosedrops or eyedrops, can relieve the symptoms of conditions due to eosinophil-associated inflammation of the nasal passages or of the eye, such as allergic rhinitis or allergic conjunctivitis.

Thus, the present invention also provides a kit comprising packaging material and a plurality of unit dosage forms of a topical anesthetic contained within said packaging material, as within an inhalor, nebulizer or metered dose inhaler; or dissolved in a liquid vehicle and contained in a bottle, said bottle optionally equipped with a cap comprising a dropper means or a spray means. Said packaging material also comprises instruction means, therein or attached thereto, instructing that one or more, e.g., about 1–4, of said unit dosage forms be administered to a human patient in order to treat bronchial asthma or one or more of the other hypersensitivity conditions discussed above. Said instruction means can be a printed label or package insert, a cassette tape, a video tape or a magnetic disk.

The present invention is based upon our finding that bronchoalveolar lavage (BAL) fluid samples obtained from a number of patients with symptomatic asthma were able to decrease eosinophil viability, below the levels found for a control fluid. This was surprising in view of the expectation that these fluid samples would contain high levels of eosinophil-associated cytokines, such as IL-5. The inhibitory factor was identified as lidocaine, which is widely employed as a topical anesthetic in BAL fluids. As discussed below, lidocaine per se was able to inhibit eosinophil-active cytokines at concentrations equivalent to those present in the BAL fluids. Furthermore, this activity was confirmed for a number of other topical anesthetics of both the benzoate and carboxamide class. Also, administration of lidocaine by inhalation was found to permit bronchial asthma patients to reduce their dependence on prednisone, indicating that lidocaine can function as a glucocortico-mimetic agent in this context.

DETAILED DESCRIPTION OF THE INVENTION

Topical Anesthetics

Figure 1:
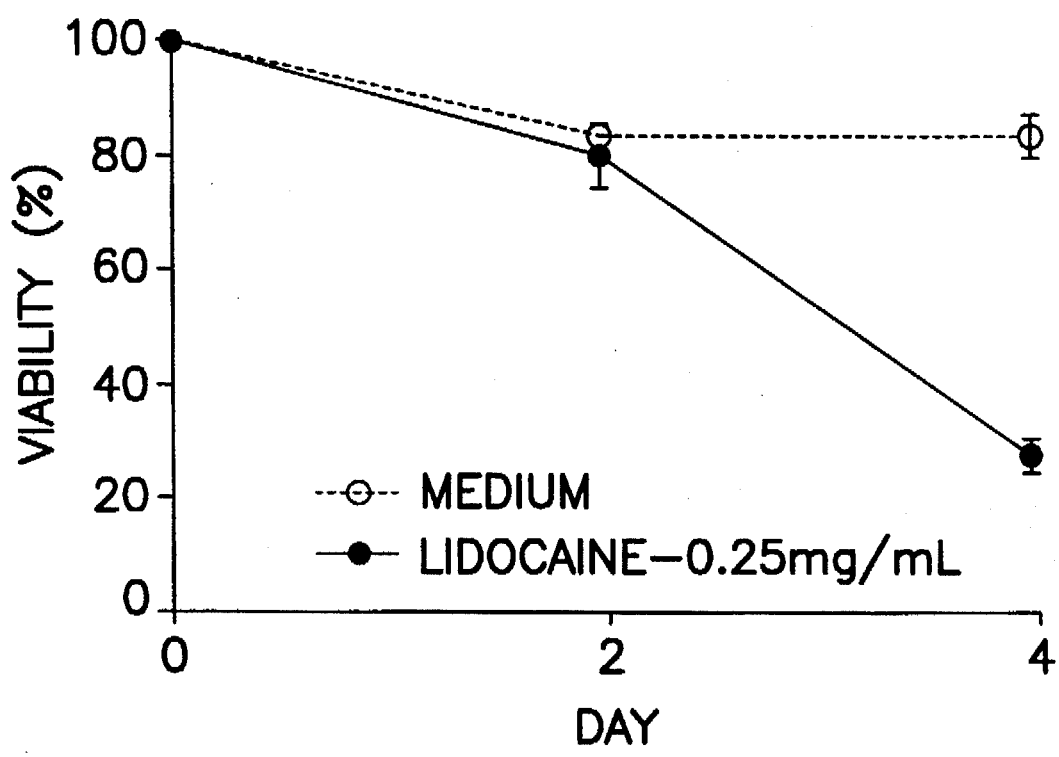
FIG. 1 is a graphical depiction of the time course of eosinophil viability inhibition effect by lidocaine. Culture medium was supplemented with recombinant human interleukin 5 (rhIL-5), 10 pg/ml, and the effects on eosinophil viability of lidocaine (0.25 mg/ml)(•), or medium control (Hybri-Care® (American Type Culture Collection, Rockville, Md.) containing gentamicin, 50 µg/ml and 10% defined calf serum (Hyclone Laboratories, Logan, Utah)) (o) were tested by comparing viabilities at two and four days.
Figure 2B:
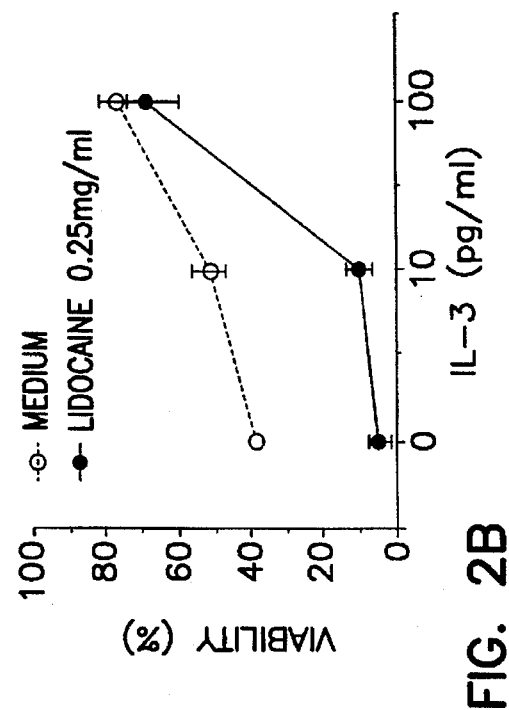
FIG. 2 is a graphical depiction of the effect of lidocaine on cytokine-mediated eosinophil survival. Lidocaine (0.25 mg/ml) (•) or medium control (o) was cultured with eosinophils ($2.5 \times 10^4$/well) and cytokines (rhIL-3) and rhIL-5), 10 and 100 pg/ml, rhGM-CSF, 2 and 20 pg/ml, rhIFN-γ, 1 and 10 U/ml, in Hybri-Care medium, total volume was 200 µl (rh=recombinant human, GM-CSF= granulocytemacrophage colony-stimulating factor, IFN-γ= gamma-interferon). After four days of culture, eosinophil viabilities were determined.
Figure 2D:
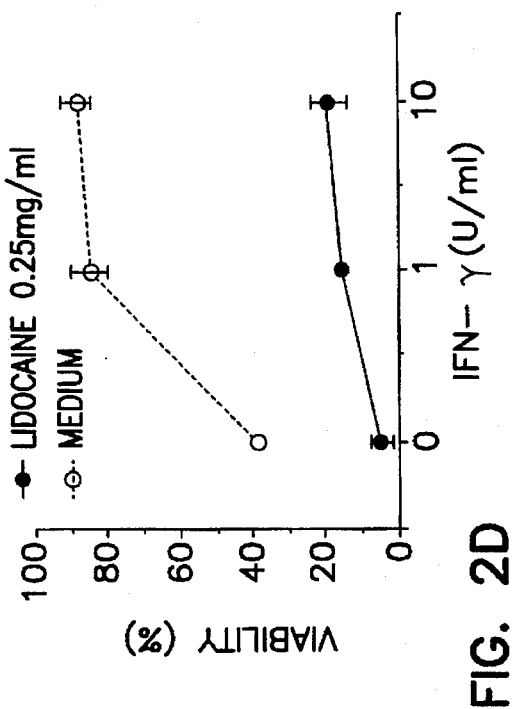
Figure 2A:
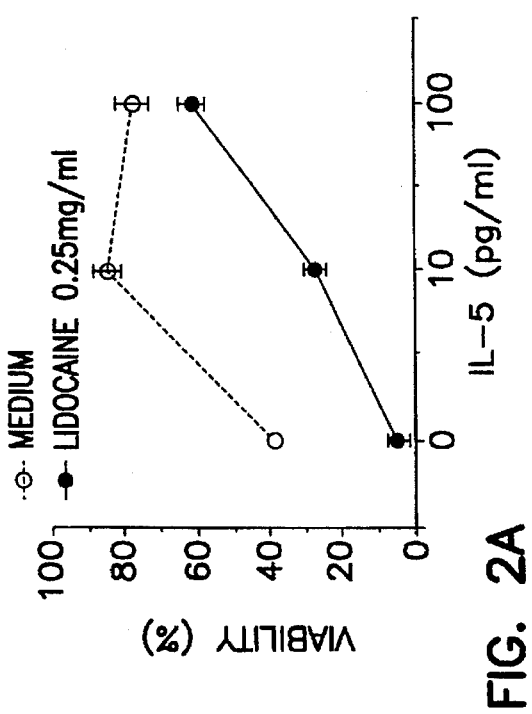
Figure 2C:
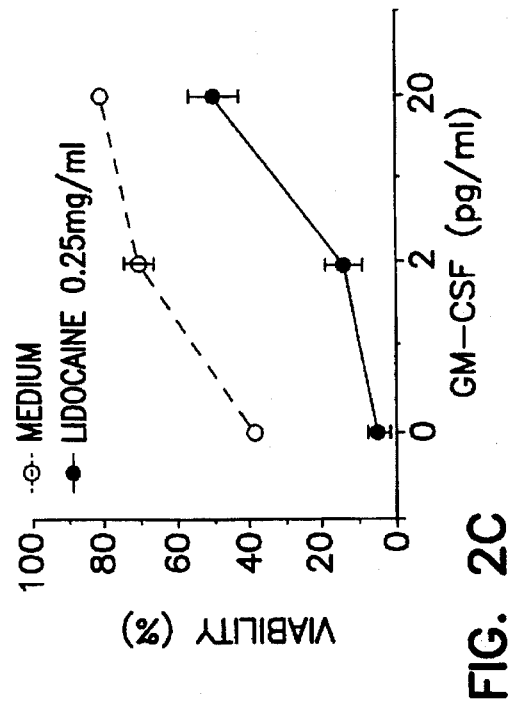

Topical anesthetics, all of which are believed to be useful in the present invention, are an art-recognized class of drugs which temporarily interrupt mammalian nerve transmissions. They can generally be grouped into two chemical classifications structurally; the N-arylamides or carboxamides, such as lidocaine; and the aminoalkylbenzoates, such as procaine, benoxinate and proparacaine. Preferred N-aryl amides comprise the N-($C_7$–$C_{22}$)arylamides of amino-substituted ($C_1$–$C_5$) carboxylic acids, e.g., N-[(mono- or di-($C_1$–$C_4$)alkyl) phenyl]amides of aliphatic ($C_1$–$C_5$)carboxylic acids, which acids are preferably substituted with the moiety (R)($R^1$)N— wherein R and $R^1$ are each ($C_1$–$C_5$)alkyl. For example, a preferred carboxylic acid can have the general formula (R)($R^1$)N(X)$CO_2$H wherein R and $R^1$ are as defined above and X is a branched- or straight-chain ($C_1$–$C_5$)alkylene group such as 1,1-ethylene, 1,2-ethylene, methylene, 2,2-propylene, 1,3-propylene, and the like. Another preferred class of N-arylamides are the N-[(mono- or di-($C_1$–$C_4$)alkyl) phenyl]amides of 5- or 6-membered-heterocycloaliphatic carboxylic acids, which acids comprise one or two [($C_1$–$C_4$) alkyl-substituted]N atoms, i.e., N-butylpiperidine-2-carboxylic acid.

The aminoalkylbenzoates include esters between benzoic acids and alcohols of the general formula ($R^4$)($R^5$)N(X)OH, wherein X is as defined above, $R^4$ is H or ($C_1$–$C_4$)alkyl, $R^5$ is ($C_1$–$C_4$)alkyl or $R^4$ and $R^5$ taken together are a 5- or 6-membered heterocycloaliphatic ring, optionally substituted by ($C_1$–$C_3$)alkyl or comprising an additional ring O- or N-atom. The benzoic acid moiety can be the moiety ($R^2$) ($R^3$)Ar$CO_2$H wherein Ar is an aromatic —$C_6H_3$— radical or "phenylene" and (phenylene) and each $R^2$ and $R^3$ is H, halo, preferably Cl, ($R^5$)(H)N—, $H_2$N— or ($C_1$–$C_5$)alkoxy.

Useful topical anesthetics include lidocaine ((2-diethylamino)-N-(2,6-dimethylphenyl)acetamide) (see Lofgren et al. (U.S. Pat. No. 2,441,498), May & Baker (British Patent No. 706409) and J. F. Macfarlane & Co. (British Patent No. 758,224)); bupivacaine (1-butyl-N-(2,6-dimethylphenyl)-2-piperidinecarboxyamide) (see Thuresson et al., (U.S. Pat. No. 2,955,111) and Sterling Drug (British Patent Nos. 1,166,802 and 1,180,712)); mepivacaine (2-piperidinecarboxyamide, N-(2,6-dimethylphenyl)-1-methyl), chloroprocaine (4-amino-2-chlorobenzoic acid 2-(diethylamino)ethyl ester); procaine (4-aminobenzoic acid 2-(diethylamino)ethyl ester); etidocaine (N-(2,6-dimethylphenyl)-2-(ethylpropylamino)butanamide; see, Astra (German Patent No. 2162744)); tetracaine (4-(butylamino)benzoic acid 2-(dimethylaminoethyl ester; see Shupe (U.S. Pat. No. 3,272,700)); benoxinate (4-amino-3-butoxybenzoic acid 2-(diethylamino)ethyl ester (U.K. Patent No. 654,484)); proparacaine (3-amino-4-propoxybenzoic acid 2-(diethylamino)ethyl ester); dibucaine (3-butoxy-N-[2-(diethylamino)ethyl]-4-quinolinecarboxyamide; Miescher (U.S. Pat. No. 1,825,623)); dyclonine (1-(4-butoxyphenyl)-3-(1-piperidinyl-1-propanone)); isobucaine (1-propanol, 2-methyl-2-[(2-methylpropyl)amino]benzoate; meprylcaine ([(2-methyl)-(2-propylamino)propyl] benzoate); piperocaine ((2-methylpiperidin-1-ylpropyl (benzoate)); prilocaine (N-(2-methylphenyl)-2-(propylamino)propanamide); propoxycaine (2-(diethylamino)ethyl-([2'-methyl-4'-amino]benzoate)); pyrrocaine (1-(pyrrolidin-1-yl)-N-(2,6-dimethylphenyl) acetamide; butacaine (((3-dibutylamino)propyl)-(2'-amionbenzoate)); cyclomethylcaine (((3-(2'-methylproperidine-1-yl))propyl)-[4'-cyclohexyloxy-benzoate]); dimethyisoquin, diperodon, hexylcaine ((([(2-cyclohexylamino)(1-methyl)]ethyl)(benzoate); proparacaine (((2-diethylamino)ethyl) [(4'-propyloxyl-3'-amino)benzoate]); cocaine and its analogs (see, F. I. Carroll et al., *J. Med. Chem.*, 34, 2719 (1991); *Eur. J. Pharmacol.*, 184, 329 (1990); and the pharmaceutically acceptable salts thereof. Preferred salts include the amine addition salts of inorganic and organic acids, e.g., the hydrochloride, hydrobromide, sulfate, oxalate, fumarate, citrate, malate, propionate and phosphate salts. The hydrochloride and sulfate salts are preferred for use in the present invention.

These topical anesthetics and the salts thereof are discussed in detail in *Remington's Pharmaceutical Sciences*, A. Osol, ed., Mack Pub. Co., Easton, Pa. (16th ed. 1980), and in *The Merck Index* (11th ed. 1989).

Administration and Dosages

While it is possible that, for use in therapy, the topical anesthetics or their salts may be administered as the pure dry chemicals, as by inhalation of a fine powder via an insufflator, it is preferable to present the active ingredient as a pharmaceutical formulation. The invention thus further provides a pharmaceutical formulation comprising one or more topical anesthetics, or pharmaceutically acceptable salts thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for administration by inhalation or insufflation or for nasal, intraocular or other topical (including buccal and sublingual) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both.

For administration to the upper (nasal) or lower respiratory tract by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator, insufflator or a metered-dose inhaler.

For intra-nasal administration, the compounds of the invention may be administered via nose drops, a liquid spray, such as via a plastic bottle atomizer or metered-dose inhaler. Typical of atomizers are the Mistometer (Wintrop) and the Medihaler (Riker).

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

For topical administration to the eye, nasal membranes or to the skin, the compounds according to the invention may be formulated as ointments, creams or lotions, or as a transdermal patch or intraocular insert. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth or throat include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

When desired, the above-described formulations adapted to give sustained release of the active ingredient may be employed, e.g., by combination with certain hydrophilic polymer matrices.

The pharmaceutical compositions according to the invention may also contain other active ingredients such as antimicrobial agents, or preservatives.

The compounds of the invention may also be used in combination with other therapeutic agents, for example, bronchodilators or anti-inflammatory agents.

It will be further appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian. In general, however, a suitable unit dose for counteracting respiratory tract symptomology will deliver from about 0.05 to about 10–15 mg/kg, e.g., from about 0.10 to about 5.0 mg/kg of body weight per day.

The desired dose may conveniently be presented in a single dose or as divided doses administered at appropriate intervals, for example, as two, three, four or more sub-doses per day. The sub-dose itself may be further divided, e.g. into a number of discrete loosely spaced administrations; such as multiple inhalations from an insufflator or by application of a plurality of drops into the eye or nose.

The invention will be further described by reference to the following detailed Example.

EXAMPLE 1

Inhibition of IL-5-Mediated Eosinophil Survival by Lidocaine

A. Eosinophil Purification

Eosinophils were purified from human peripheral blood, as previously described by T. Fujisawa et al., *J. Immunol.*, 144, 642 (1990). Briefly, heparinized (10 U/ml) venous blood was obtained from normal volunteers or patients with mild asthma or hay fever and sedimented with 6% dextran in 0.9% NaCl (Gentran 70) (Travenol Laboratories, Deerfield, Ill.) at 5:1 (v/v) ratio for 45 minutes at 37° C. The buffer coat was collected and washed twice in Pipes buffer (25 mM piperazine-N,N'-bis[2-ethanesulfonic acid]), 110 mM NaCl, 5 mM KCl, 25 mM NaOH, 5.4 mM glucose, pH 7.4) with 50 U/ml DNase (Sigma Chemical Co., St. Louis, Mo.). The cells were suspended in 2.4 ml of Percoll (Sigma), density 1.070 g/ml, with 5% heat-inactivated defined calf serum (DCS) (Hyclone Laboratories, Logan, Utah) and overlayered on a discontinuous Percoll gradient consisting of the following densities (g/ml): 1,080, 1,085, 1.090, 1.100, and 1.120. The osmolarity of Percoll ranged from 290 to 315 mOsm/kg and the pH was 7.4. Cells were centrifugated through the gradient at 1,500 g in a JA-20 fixed angle rotor on a Beckman J2-21 centrifuge at 4° C. for 45 minutes. Fractions were collected and eosinophil numbers were determined utilizing Randolph's stain. Eosinophil-rich fractions were pooled, washed twice in Pipes buffer with 1% DCS, and used for experiments immediately. The eosinophil preparations were >80% pure and >98% viable, as determined by Randolph's stain and by trypan blue exclusion, respectively. The contaminating cells were neutrophils. There was no contamination by lymphocytes or monocytes.

B. Eosinophil Survival Assay

Eosinophils were cultured at 37° C. and 5% $CO_2$ in 200 µl Hydri-Care medium containing gentamicin and 10% DCS in 90-well, flat-bottom tissue culture plates at a cell concentration of $2.5 \times 10^5$/ml or $1.25 \times 10^5$ cells/ml. No difference in viability was observed at these two cell concentrations. Viability was determined at day 4 for all experiments unless otherwise specified. A Neubauer hemacytometer (C. A. Hausser & Son; Philadelphia, Pa.) and fluorescence microscopy were used to count live cells, stained green with fluorescein diacetate (B. Rotman et al., *PNAS USA*, 55, 134 (1966)), and dead cells, stained red with propidium iodide (G. R. Pullen et al., *J. Immunol. Methods*, 43, 87 (1981)). Viability was calculated by the formula: viability, %=(live cells)/(live cells+dead cells))×100%. Each experiment was performed in duplicate and all results represent three or more experiments.

C. Cytokine-mediated Eosinophil Survival and Effects of Topical Anesthetics

As reported by N. Wallen et al., *J. Immunol.*, 147, 3940 (1991), the responses of eosinophil survival to increasing concentrations of IL-5, IL-3, GM-CSF and IFN-γ were determined. For determination of the effect of lidocaine and other topical anesthetics on cytokine-mediated survival, eosinophils were cultured in the presence of specified cytokine and topical anesthetic concentrations, and viability in the presence of the test anesthetic was compared to viability in cytokine-enriched medium alone. Anesthetics were dissolved in 0.15M NaCl, stored at −20° C., and diluted in medium just before use; thus, 0.15M NaCl was used as a control for each experiment. The effects of the anesthetics and the vehicle control on cytokine-mediated viability were tested. Inhibition of viability was determined by the formula: inhibition, %=$(V_{med}-V_{an})/V_{med} \times 100\%$, where $V_{med}$= viability in cytokine-enriched medium alone and $V_{an}$= viability at the specified anesthetic and cytokine concentrations. $IC_{50}$ is the concentration of anesthetic that produces 50% inhibition of viability. The change in dose-response to cytokine in the presence of varied lidocaine concentrations was tested and the $EC_{50}$ for each lidocaine concentration was calculated. $EC_{50}$ is the IL-5 concentration that produces 50% enhancement of viability; the 50% viability enhancement was determined by subtracting the baseline viability from the maximum viability and dividing the difference by two, or $V_{50}=(V_{max}-V_{min})/2+V_{min}$, where $V_{max}$=viability achieved with optimum cytokine concentration and $V_{min}$=viability in the absence of cytokine and anesthetic. For determination of the time course of the anesthetic effect, medium was supplemented with rIL-5, 220 fM, or 890 fM, and the effects of anesthetic 1000 nM, 100 nM, or control were tested by comparing viability at 1, 2, and 4 days in the presence or absence of anesthetic.

D. Statistics

All values are expressed at the mean±SEM and represent three or more experiments performed in duplicate. Significance of differences in viability were determined using a one-tailed Student's t-test.

E. Results

As shown in FIG. 1, when 10 pg/ml IL-5 was used in eosinophil culture, significant inhibition by lidocaine was not seen until day 4 of incubation. Second, as shown in FIG. 2, the eosinophil survival inhibition produced by lidocaine was overcome by high concentrations of cytokines, except for IFN-γ.

EXAMPLE 2

Inhibition of Eosinophils by Local Anesthetics

To determine whether or not other topical anesthetics, particularly those of the carboxamide (lidocaine) class or benzoate class, also can inhibit eosinophil viability in vitro, the assay of Example 1(c) was carried out. Eosinophils were cultured in the presence of 100 pg/ml IL-5 and 1 mM/ml, 0.1 mM/ml and 0.01 mM/ml of lidocaine and nine other topical anesthetics, and viability in the presence of the anesthetic was compared to viability in medium with and without IL-5. The results of this study are summarized on Table 1, below.

TABLE I

| IL-5 | Local Anesthetic, 1 mM/ml | Viable Eosinophils on Day 4 ($\bar{X} \pm SD$) |
|---|---|---|
| 100 pg/ml | Lidocaine | 10 ± 2 |
| 100 pg/ml | Bupivacaine | 0 ± 0 |
| 100 pg/ml | Chloroprocaine | 54 ± 13 |
| 100 pg/ml | Etidocaine | 0 ± 0 |
| 100 pg/ml | Procaine | 59 ± 22 |
| 100 pg/ml | Tetracaine | 0 ± 0 |
| 100 pg/ml | Benoxinate | 0 ± 0 |
| 100 pg/ml | Proparacaine | 27 ± 8 |
| 100 pg/ml | Dibucaine | 0 ± 0 |
| 100 pg/ml | Dyclonine | 0 ± 0 |
| 100 pg/ml | None | 78 ± 8 |
| 10 pg/ml | None | 69 ± 7 |
| None | None | 22 ± 11 |

As described above, in the eosinophil survival assay, eosinophils are cultured in the absence and the presence of a survival stimulating factor, such as interleukin (IL)-5. In Table 1, eosinophil viability was enhanced over culture medium by addition of 10 or 100 pg/ml of IL-5. For example, the survival of eosinophils in the absence of any survival-enhancing factor was 22% (78% of the eosinophils were dead) at four days. In the presence of IL-5, the survival of eosinophils was increased to 78% by 100 pg/ml of IL-5. In the presence of 100 pg/ml of IL-5, 1 mM of lidocaine inhibited eosinophil survival, such that only 10% of the cells were viable at day 4. Similarly, bupivacaine, etidocaine, tetracaine, benoxinate, dibucaine and dyclonine strikingly inhibited eosinophil survival, suggesting that they were as potent, if not more potent, than lidocaine. In addition, proparacaine also showed weak IL-5 inhibitory activity reducing eosinophil survival from an expected 78% (in the presence of IL-5, 100 pg/ml) to 27%. These data indicate that numerous topical anesthetics have potent effects on eosinophil survival and appear to exhibit a bioactivity which is comparable to that exhibited by lidocaine.

EXAMPLE 3

Treatment of Bronchial Asthma with Lidocaine

Glucocorticoids are believed to be effective to manage bronchial asthma due to their ability to interfere with the cytokine-indicated accumulation and activation of inflammatory cells, including eosinophils. Examples 1–2 indicate that lidocaine and other topical anesthetics are able to mimic the bioactivity of glucocorticoids. Therefore, lidocaine was evaluated for its ability to replace glucocorticoids in the therapy of bronchial asthma.

A. Patient A

Patient A is a woman (age 43) presenting with chronic, severe, glucocorticoid-dependent bronchial asthma. This patient was begun on lidocaine inhalation (2% aqueous lidocaine, 2 ml per nebulization, four times a day) delivered via a deVilbiss nebulizer (Model #5610D). Nebulization of this concentration of lidocaine has not caused side effects other than transient numbness of the oral cavity and of the upper regions of the pharynx and larynx, and this was well tolerated.

Figure 3A:
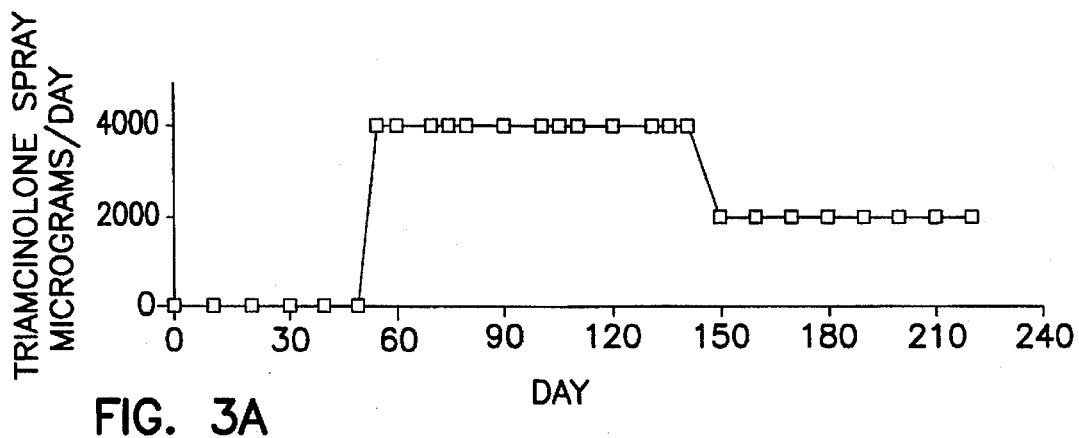
FIG. 3 is a graphical depiction of the drug regimen of Patient A with respect to triamcinolone (Panel A), lidocaine (Panel B) and prednisone (Panel C).
Figure 3B:
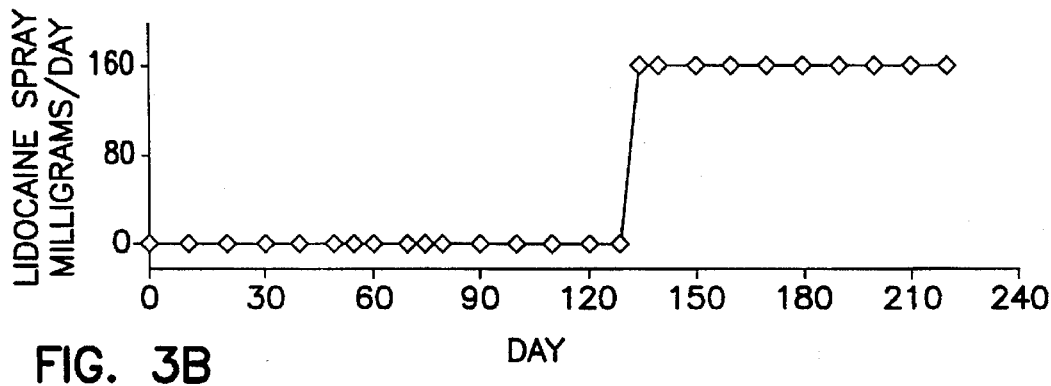
Figure 3C:
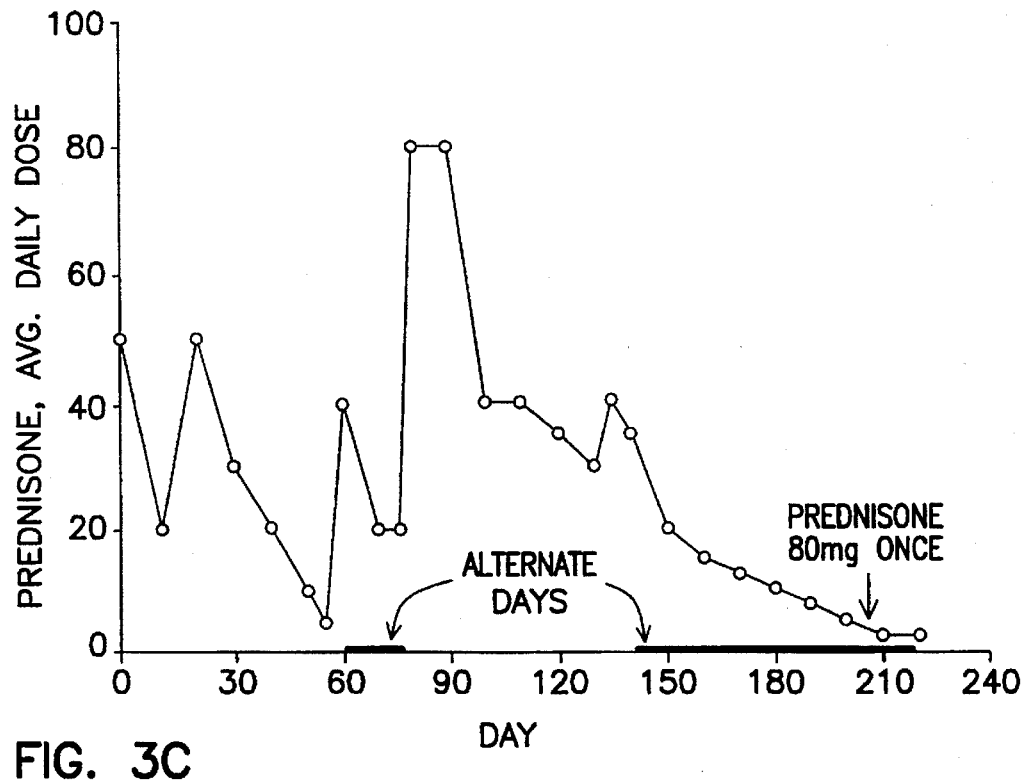

Patient A was begun on lidocaine inhalation in early September 1992, at a time when she was receiving 40 mg of prednisone orally a day, as well as 20 puffs of asthmacort (triamcinolone). Over the preceding four months, the patient had received virtually continuous prednisone therapy. The lowest dose administered was 5 mg daily for a period of a few days in the middle of June 1992. After that reduction in therapy, the patient required a prompt increase in the quantity of glucocorticoids to 40 mg daily and then a taper was done such that she received 40 mg on one day and decrease in prednisone on the alternate day. As shown on FIG. 3, the patient eventually reached a dose of 20 mg prednisone on one day and no prednisone on the following day, but this regimen was followed by a severe flare of asthma, such that for a period of time in July, she required therapy with 80 mg of prednisone a day.

Initiation of lidocaine therapy in late September was associated with a reduction in the patient's nocturnal cough and with relief of the patient's breathlessness. The prior prednisone therapy, while keeping the asthma under control, did not completely relieve the symptoms, whereas lidocaine therapy was associated with a feeling of well being and virtually complete relief of symptoms. Following initiation of lidocaine therapy, the patient's prednisone was reduced gradually, such that by December 1992, the patient was receiving 5 mg every other day, a dose which she had not been able to achieve other than briefly in June 1992. In mid-November, an exacerbation of asthma occurred following a respiratory tract infection, which was treated by addition to the patient's therapy of one administration of 80 mg of prednisone.

B. Patient B

Figure 4A:
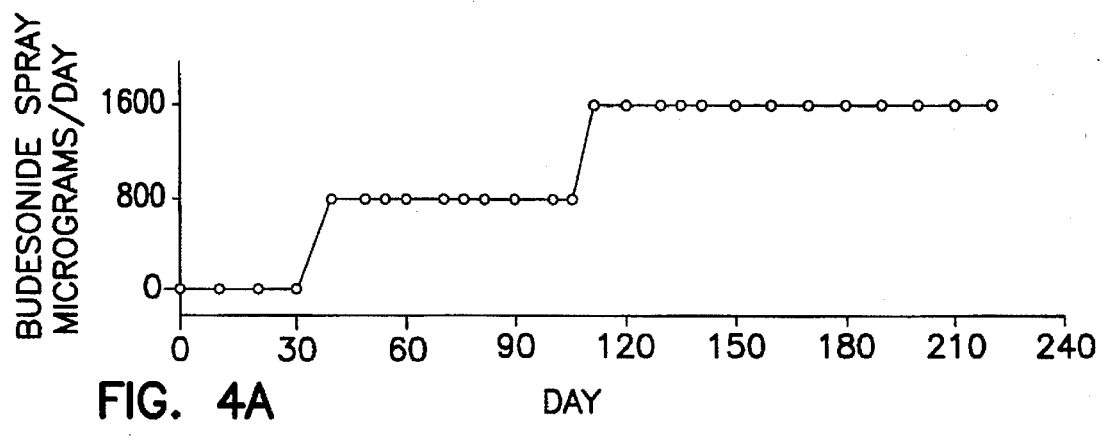
FIG. 4 is a graphical depiction of the drug regimen of Patient B with respect to budesonide (Panel A), lidocaine (Panel B) and prednisone (Panel C).
Figure 4B:
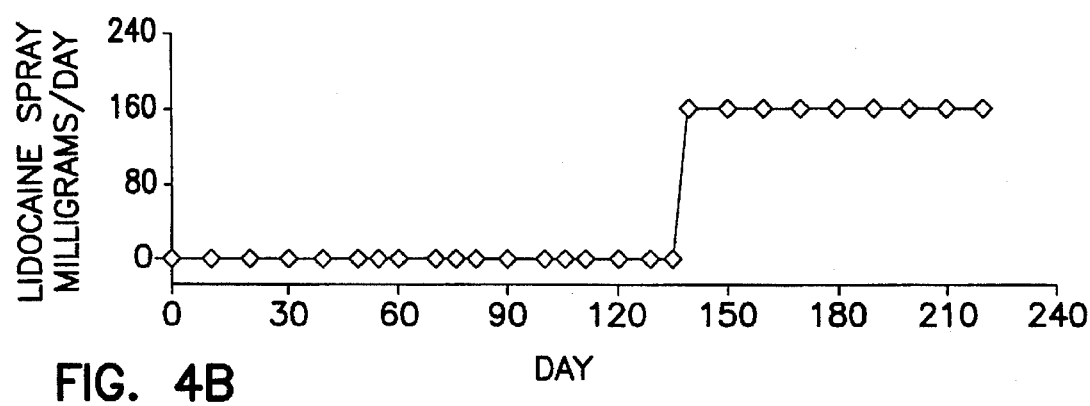
Figure 4C:
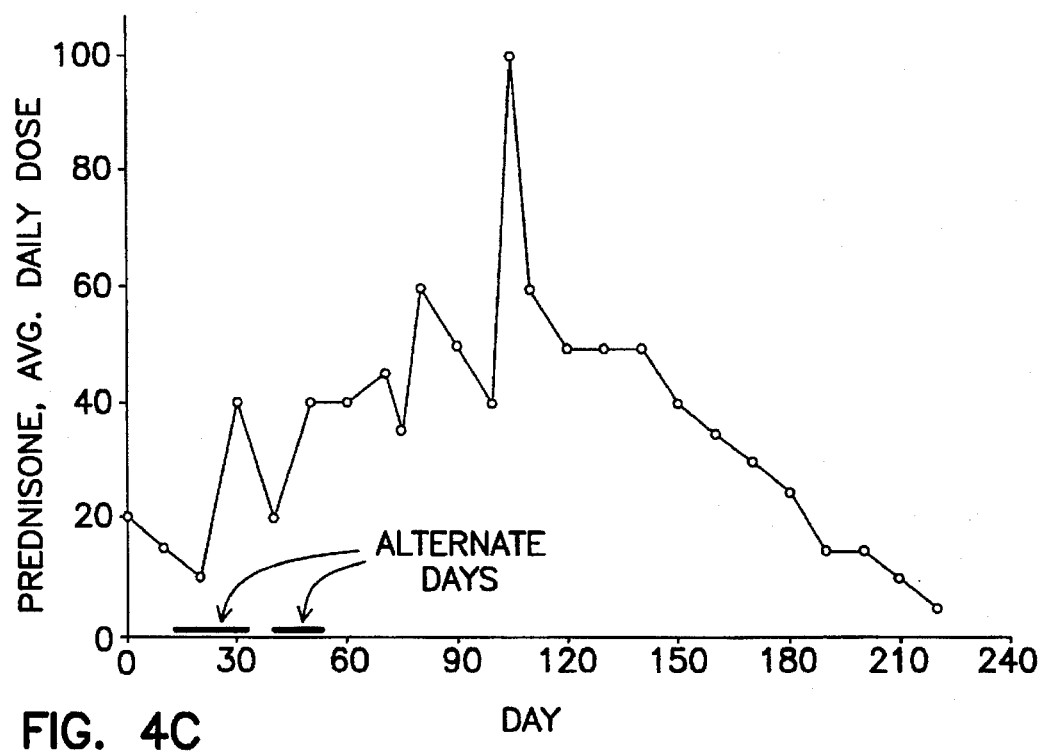

Patient B is a woman (age 34), who was begun on lidocaine therapy around the middle of September 1992, as described in section A, above. As shown by FIG. 4, she has been able to reduce prednisone therapy from an average of 50 mg daily to a dose of 5 mg daily in early December 1992. This reduction has not been associated with any untoward effects other than those which one anticipates from reduction of glucocorticoids in any patient who has been receiving glucocorticoids for long periods of time. (Glucocorticoid withdrawal causes a characteristic syndrome associate with malaise and muscle aching; both patients A and B have experienced these symptoms).

All publications and patents are herein incorporated by reference to the same extent as if each individual publication or patent application was specifically and individually indicated to be incorporated by reference. Specifically, the literature and patents incorporated by reference in the section on "Topical Anesthetics" are incorporated for their teaching of analogs, salts and derivatives of the anesthetics specifically disclosed herein, which can also be used in the present invention.

It will be apparent to one of ordinary skill in the art that many changes and modifications can be made in the invention without departing from the spirit or scope of the appended claims.

What is claimed is:

1. A method for treating an eosinophil-associated disease consisting essentially of administering to a human afflicted with said disease an amount of a topical anesthetic effective to counteract the symptoms of said disease by inhibiting the activity of eosinophil-active cytokines, wherein the disease is selected from the group consisting of intranasal inflammation, nasal polyps, paranasal sinus inflammation, allergic rhinitis, ocular inflammation, vernal conjunctivitis, allergic conjunctivitis, and dermal inflammation, and the topical anesthetic is bupivacaine, dibucaine, an N-arylamide, an ester between a carboxylic acid of the general formula:

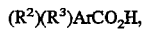

$$(R^2)(R^3)ArCO_2H,$$

wherein Ar is $C_6H_3$ and each $R^2$ and $R^3$ is H, halo, $(R^1)(H)N-$ wherein $R^1$ is $(C_1-C_5)$alkyl, $H_2N-$, or $(C_2-C_5)$ alkoxy; and an alcohol of the general formula:

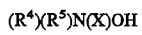

$$(R^4)(R^5)N(X)OH$$

wherein X is a $(C_1-C_5)$ branched- or straight-chain alkylene; $R^4$ is H or $(C_1-C_4)$alkyl, $R^5$ is $(C_1-C_4)$alkyl or $R^4$ and $R^5$ taken together can be a 5- or 6-membered heterocycloaliphatic ring, optionally substituted by $(C_1-C_3)$alkyl or comprising an additional ring O- or N-atom; or a pharmaceutically acceptable salt thereof.

2. The method of claim 1 wherein the topical anesthetic is administered to the respiratory tract of the human by spraying or nebulization.

3. The method of claim 1 wherein the topical anesthetic is administered in combination with a pharmaceutically acceptable liquid vehicle.

4. The method of claim 1 wherein the topical anesthetic is administered at a daily dose of about 0.05–15 mg/kg.

5. The method of claim 1 wherein the topical anesthetic is an $N-(C_7-C_{22})$ arylamide of an amino substituted $(C_1-C_5)$-carboxylic acid or a pharmaceutically acceptable salt thereof.

6. The method of claim 5 wherein the topical anesthetic is an N-[mono- or di-$(C_1-C_4)$alkyl)phenyl]amide of an aliphatic $(C_1-C_5)$carboxylic acid, wherein said acid is substituted with (R)(R')N—, wherein R is H or $(C_1-C_5)$-alkyl and R' is $(C_1-C_5)$alkyl; or a pharmaceutically acceptable salt thereof.

7. The method of claim 6 wherein the topical anesthetic is lidocaine, prilocaine, etidocaine or a pharmaceutically acceptable salt thereof.

8. The method of claim 7 wherein the topical anesthetic is lidocaine or lidocaine hydrochloride.

9. The method of claim 1 wherein the topical anesthetic is procaine, chloroprocaine, dyclonine, tetracaine, benoxinate, proparacaine, meprylcaine, piperocaine or a pharmaceutically acceptable salt thereof.

10. A method for treating bronchial asthma comprising administering by spraying or by nebulization, to the respiratory tract of a human afflicted with bronchial asthma and subjected to extended steroid therapy, an amount of a topical anesthetic effective to counteract the symptoms of said bronchial asthma, and to gradually reduce the dependence of said human or chronic steroid therapy, wherein the topical anesthetic is administered at a daily dose of about 2.0–15 mg/kg, and wherein the topical anesthetic is an aminoalkylbenzoate or a pharmaceutically acceptable salt thereof.

11. The method of claim 10 wherein the topical anesthetic is administered in combination with a pharmaceutically acceptable liquid vehicle.

12. The method of claim 10 wherein the topical anesthetic is an ester between a carboxylic acid of the general formula:

$$(R^2)(R^3)ArCO_2H,$$

wherein Ar is $C_6H_3$ and each $R^2$ and $R^3$ is H, halo, $(R^1)(H)N-$ wherein $R^1$ is $(C_1-C_5)$alkyl, $H_2N-$, or $(C_2-C_5)$ alkoxy; and an alcohol of the general formula $$(R^4)(R^5)N(X)OH$$

wherein X is a $(C_1-C_5)$ branched- or straight-chain alkylene; $R^4$ is H or $(C_1-C_4)$alkyl, $R^5$ is $(C_1-C_4)$alkyl or $R^4$ and $R^5$ taken together can be a 5- or 6-membered heterocycloaliphatic ring, optionally substituted by $(C_1-C_3)$alkyl or comprising an additional ring O- or N-atom, and the pharmaceutically acceptable salts thereof.

13. The method of claim 12 wherein the topical anesthetic is procaine, chloroprocaine, dyclonine, tetracaine, benoxinate, proparacaine, meprylcaine, piperocaine or a pharmaceutically acceptable salt thereof.

14. A method for treating bronchial asthma comprising administering by spraying or by nebulization to the respiratory tract of a human afflicted with bronchial asthma and subjected to extended steroid therapy, an amount of a topical anesthetic effective to counteract the symptoms of said bronchial asthma, and to gradually reduce the dependence of said human on chronic steroid therapy, wherein the topical anesthetic is administered at a daily dose of about 2.0–15 mg/kg, and wherein the topical anesthetic is selected from the group consisting of bupivacaine, dibucaine and a pharmaceutically acceptable salt thereof.

15. The method of claim 14 wherein the topical anesthetic is administered in combination with a pharmaceutically acceptable liquid vehicle.

* * * * *